United States Patent [19]

McEwen et al.

[11] 4,427,813

[45] * Jan. 24, 1984

[54] POLYCARBONATE CONTAINING A BIS(CYCLIC PHOSPHATE) AS A THERMAL STABILIZER

[75] Inventors: Gerald K. McEwen; Lowell S. Thomas, both of Midland, Mich.

[73] Assignee: The Dow Chemical Co., Midland, Mich.

[*] Notice: The portion of the term of this patent subsequent to Mar. 3, 1998 has been disclaimed.

[21] Appl. No.: 330,752

[22] Filed: Dec. 14, 1981

[51] Int. Cl.$^3$ ............................. C08K 5/52; C07F 9/15
[52] U.S. Cl. ................................. 524/119; 260/927 R; 524/119
[58] Field of Search ...................... 260/927 R; 524/119

[56]     References Cited
U.S. PATENT DOCUMENTS

| 2,859,086 | 11/1958 | Feild, Jr. et al. | 260/927 R |
| 2,880,225 | 3/1959 | Lanham | 260/927 R |
| 3,890,409 | 6/1975 | Mayerhoefer et al. | 260/927 R |
| 4,035,448 | 7/1977 | Mayerhoefer et al. | 260/930 |
| 4,049,617 | 9/1977 | Albright | 260/927 R |
| 4,143,101 | 3/1979 | Mayerhoefer et al. | 260/927 R |
| 4,178,281 | 12/1979 | Horn, Jr. | 260/45.8 R |
| 4,254,014 | 3/1981 | McEwen et al. | 260/927 R |

Primary Examiner—Anton H. Sutto

[57]     ABSTRACT

A polycarbonate such as a bisphenol-A homopolycarbonate containing a small amount of an aromatic bis(cyclic phosphate) such as 2,2'-[(1-methylethylidene)-bis(4,1-phenyleneoxy-2,1-ethanediyloxy)]bis(5,5-dimethyl-2,2'-dioxo-1,3,2-dioxaphosphorinane) exhibits improved thermal stability.

8 Claims, No Drawings

POLYCARBONATE CONTAINING A BIS(CYCLIC PHOSPHATE) AS A THERMAL STABILIZER

BACKGROUND OF THE INVENTION

This invention relates to polycarbonates containing additives which increase the thermal stability thereof.

Polycarbonates derived from reactions of dihydroxyorganic compounds, particularly the dihydric phenols, and carbonic acid derivatives such as phosgene have found extensive commercial application because of their excellent physical properties. These thermoplastic polymers appear to be particularly suitable for the manufacture of molded parts wherein impact strength, rigidity, toughness, heat resistance and excellent electrical properties are required.

It is found, however, that the polycarbonates exhibit poor thermal stability. Heretofore in order to improve thermal stability of the polycarbonate, cyclic phosphites have been added to the polycarbonate. Unfortunately, such phosphites deleteriously affect the hydrolytic stability of the polycarbonate.

In view of the deficiencies of many of the conventional polycarbonate compositions, it is highly desirable to provide a polycarbonate composition having improved thermal stability without adversely affecting other properties of the polycarbonate such as hydrolytic stability, tensile and impact strength, and molecular weight.

SUMMARY OF THE INVENTION

In one aspect, the present invention is a polycarbonate composition comprising a carbonate polymer having dispersed therein an aromatic bis(dioxodioxaphosphorinane), an aromatic bis(dithiodioxaphosphorinane), or an aromatic bis(oxothiodioxaphosphorinane) in an amount sufficient to measurably increase the thermal stability of the carbonate polymer. Hereinafter, such composition shall be referred to as a stabilized polycarbonate and the three aforementioned aromatic bis-phosphorinanes shall be referred to as the bis(di-Y-dioxaphosphorinanes). The stabilized polycarbonate of the present invention exhibits good processability, e.g., good melt flowability; thermal stability, i.e., resists discoloration and weight loss upon exposure to high temperatures; and hydrolytic stability, i.e., resists molecular weight loss upon exposure to water.

In another aspect, the present invention is a bis(di-Y-dioxaphosphorinane) which is useful as a thermal stabilizer aid in polycarbonates.

The stabilized polycarbonate of the present invention is suitably employed in most applications which polycarbonates have been previously utilized. Applications of particular interest for the utilization of the stabilized polycarbonates of this invention are as follows: automobile parts, e.g., air filters, fan housings, exterior components; housing for electrical motors, appliances, business and office equipment, and photographic equipment, lighting and aircraft applications.

DETAILED DESCRIPTION OF THE EMBODIMENTS

The polycarbonates employed in the present invention are advantageously aromatic carbonate polymers such as the trityl diol carbonates described in U.S. Pat. Nos. 3,306,036; 3,036,037; 3,036,038 and 3,036,039; polycarbonates of bis(ar-hydroxyphenyl)alkylidenes (often called bisphenol-A type diols) including their aromatically and aliphatically substituted derivatives such as disclosed in U.S. Pat. Nos. 2,999,835; 3,028,365 and 3,334,154; and carbonate polymers derived from other aromatic diols such as described in U.S. Pat. No. 3,169,121.

It is understood, of course, that the polycarbonate may be derived from (1) two or more different dihydric phenols or (2) a dihydric phenol and a glycol or a hydroxy- or acid-terminated polyester or a dibasic acid in the event a carbonate copolymer or interpolymer rather than a homopolymer is desired. Also suitable for the practice of this invention are blends of any one of the above carbonate polymers. Also included in the term "carbonate polymer" are the ester/carbonate copolymers of the types described in U.S. Pat. Nos. 3,169,121; 4,287,787; 4,156,069; 4,260,731 and 4,105,633. Of the aforementioned carbonate polymers, the polycarbonates of bisphenol-A and derivatives, including copolycarbonates of bisphenol-A, are preferred. Methods for preparing carbonate polymers for use in the practice of this invention are well-known, for example, several suitable methods are disclosed in the aforementioned patents which are hereby incorporated by reference in their entirety.

The aromatic bis(di-Y-dioxaphosphorinane) of the present invention is advantageously represented by the formula:

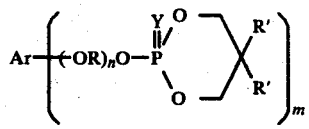

wherein Ar is an aromatic radical having each of its valences (valence bonds) on an aromatic ring; each Y is individually sulfur or oxygen; each R is individually a divalent aliphatic radical; n is 0 or a whole number up to 10, preferably 2 to 4, most preferably 2; m is a whole number from 1 to 3, preferably 1 or 2, most preferably 2; and each R' is individually hydrogen or a monovalent organic radical provided that the aromatic bis(di-Y-dioxaphosphorinane) does not adversely affect the properties of the polycarbonate under conditions of fabrication and use. Exemplary Ar includes phenylene or aromatically substituted phenylene wherein the substituent(s) halo, alkyl, aryl, amino, etc.; bis(phenylene)alkanes such as 2,2-bis(4-phenylene)propane and halogenated 2,2-bis(4-phenylene)propane such as 2,2-bis(ar, ar-dibromo-4-phenylene)propane; bis(phenylene)oxides and bis(phenylene)sulfides; and the like, with the bis(phenylene)alkanes, especially 2,2-bis(4-phenylene)propane (derived from bisphenol-A), being preferred. Exemplary R includes alkylene, e.g., ethylene and propylene; alkyleneoxyalkylene, alkylenethioalkylene, poly(alkyleneoxy)alkylene, poly(alkylenethio)alkylene, arylene and the like, with alkylene, especially ethylene, being preferred. Exemplary R' includes hydrogen, alkyl, and haloalkyl, with alkyl, especially methyl, being preferred. Y is preferably oxygen and n is preferably 0, 1 or 2.

Examples of preferred aromatic bis(di-Y-dioxaphosphorinanes) include 2,2'-[(1-methylethylidene) bis(4,1-phenyleneoxy-2,1-ethanediyloxy)]bis(5,5-dimethyl-2,2'-dioxo-1,3,2-dioxaphosphorinane). Examples of suitable, but less preferred, bis(di-Y-dioxaphosphorinanes) are 2,2'-[(1-methylethylidene)bis(4,1-phenyleneoxy-2,1- ethanediyloxy)]bis(5,5-dimethyl-2,2'-dithio-1,3,2-dioxaphosphorinane) and 2,2'-[(1-methylethylidene)bis(4,1-phenyleneoxy-2,1-ethanediyloxy))]bis(5,5-dimethyl-2-oxo-2'-thio-1,3,2-dioxaphosphorinane).

The aromatic bis(di-Y-dioxaphosphorinanes) employed in the practice of the present invention are readily prepared by converting the corresponding aromatic bis(dioxaphosphorinane) via oxidation or thiooxydation to the desired aromatic bis(di-Y-dioxaphosphorinane). The aromatic bis(dioxaphosphorinane) is made by reacting a halo (dioxaphosphorinane) of the formula:

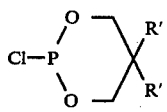

with a diol of the formula:

HOROArOROH in the presence of an amine catalyst such as triethylamine or similar trialkyl amine. The halo(dioxaphosphorinane) is advantageously produced by reacting phosphorus trichloride with pentaerythritol or similar suitable diol. See, for example, the procedure described by R. S. Edmundson, Chem. Ind. (London) 27, 1220 (1965).

The stabilized polycarbonate of the present invention is suitably prepared by combining the carbonate polymer with an effective amount of aromatic bis(di-Y-dioxaphosphorinane) (stabilizer) using any one of a variety of blending procedures conventionally employed for incorporating additives into carbonate polymer resins. For example, dry particulates of the carbonate polymer and the stabilizer may be dry blended and the resulting dry blend extruded into the desired shape.

While any amount of the stabilizer that imparts to the polycarbonate an improved resistance to degradation upon exposure to heat is suitable, preferred amounts of the stabilizer are in the range from about 0.001 to about 1, especially from about 0.005 to about 0.05, weight percent based on the weight of the carbonate polymer.

In addition to the aforementioned aromatic bis(di-Y-dioxaphosphorinane), other additives may be included in the stabilized polycarbonate of the present invention such as fillers, pigments, dyes, antioxidants, stabilizers, ultraviolet light absorbers, mold release agents and other additives commonly employed in polycarbonate resin formulations.

The following examples are given to further illustrate the invention and should not be construed as limiting its scope. In the following examples, all parts and percentages are by weight unless otherwise indicated.

EXAMPLE 1

A. Preparation of 2,2'-[(1-methylethylidene)bis(4,1-phenyleneoxy-2,1-ethanediyloxy)]bis(5,5-dimethyl-2,2'-dioxo-1,3,2-dioxaphosphorinane) (Stabilizer A)

To a 2-liter, 3-necked round bottom flask equipped with stirrer, nitrogen purge and addition funnel is added 137.5 g (1 mole) of PCl₃ dispersed in 100 ml of methylene chloride. A solution of 104 g (1 mole) of neopentylglycol [(CH₃)₂C(CH₂OH)₂] in 250 ml of methylene chloride is then added dropwise to the flask over a period of one hour. The reaction mixture is stirred for an additional 1.5 hours at 25° C. The reaction mixture contains 1-chloro-5,5-dimethyl-1,3,2-dioxaphosphorinane, i.e.,

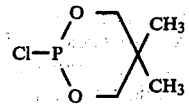

This product is transferred to the addition funnel and the flask is charged with 158 g (0.5 mole) of the diethylene glycol adduct of bisphenol-A,

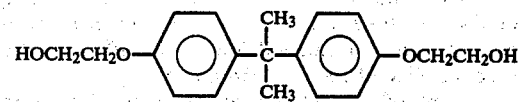

suspended in 250 ml of methylene chloride and 101 g (1 mole) of triethylamine. The stirred suspension is cooled to −10° C. and the chlorocyclic phosphorinane is added dropwise to the suspension. After the addition is complete, the flask is heated to room temperature and stirred for three hours. The reaction product is filtered to remove triethylamine hydrochloride and then stripped of solvent on a rotary evaporator. The desired aromatic bis(dioxaphosphorinane) represented by the formula:

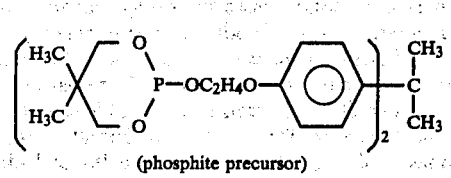

(phosphite precursor)

is recovered as a viscous liquid in a yield of 266 g.

To 10.0 g (0.017 mole) of this phosphite precursor dissolved in 50 ml of methylene chloride is added incrementally with stirring 5.95 g (0.34 mole) of m-chloroperbenzoic acid. After the addition is complete, the resulting solution is cooled to room temperature and the precipitated benzoic acid is removed by filtration. The methylene chloride is removed by evaporation under vacuum, and the resulting residue is redissolved in acetone and diluted with ether. This solution is cooled to −10° C. yielding finely divided white crystals which are filtered, washed and dried. Analysis of the crystals indicates them to be as follows:

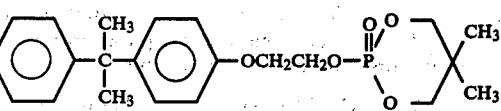

2,2'-[(1-methylethylidene)bis(4,1-phenyleneoxy-2,1-ethanediyl)]bis(5,5-dimethyl-2,2'-dioxo-1,3,2-dioxaphosphorinane) (Stabilizer A).

B. Preparation of 2,2'-[(1-methylethylidene)bis(4,1-phenyleneoxy-2,1-ethanediyloxy)]bis(5,5-dimethyl-2,2'-dithio-1,3,2-dioxaphosphorinane) (Stabilizer B)

Into a 200 ml round bottom flask is charged 40 g (0.069 mole) of the aforementioned phosphite precursor and 4.41 g (0.138 mole) of sulfur. These reactants are heated under nitrogen with stirring to 90° C. at which point the reaction becomes exothermic thereby increasing the temperature of the reaction mixture of ~130° C. The reaction mixture is cooled to room temperature and then diluted with 200 ml of diethyl ether and 10 ml of acetone. The resulting yellow solution is cooled in a dry ice/acetone bath causing the formation of white crystals in a viscous liquid. The reaction mixture is warmed to room temperature at which point the viscous liquid redissolves leaving the white crystals which are filtered, washed and dried. Analysis of the crystals indicates the material to be as follows:

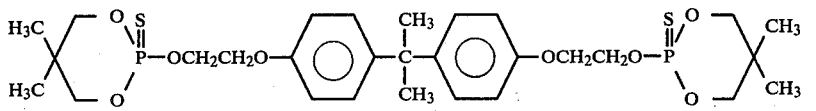

2,2'-[(1-methylethylidene)bis(4,1-phenyleneoxy-2,1-ethanediyl)]bis(5,5-dimethyl-2,2'-dithio-1,3,2-dioxaphosphorinane) (Stabilizer B).

C. Preparation of 2,2'-[(1-methylethylidene)bis(4,1-phenyleneoxy)]-bis(5,5-dimethyl-2,2'-dioxo-1,3,2-dioxaphosphorinane) (Stabilizer C)

Into a 500-ml round bottom flask fitted with a condenser, stirrer, and $N_2$ inlet is placed 307 g phosphonyl chloride ($OPCl_3$) (1 mole), 45.6 g bisphenol A (0.2 mole) and 1.5 g potassium chloride catalyst. The system is connected to an acid scrubber and heated to reflux (≅105° C.) for 24 hours. The excess $OPCl_3$ is then distilled off, first at atmospheric pressure and then under vacuum. The residue is cooled to room temperature and 200 ml tetrahydrofuran is added to the flask with stirring along with 41.6 g neopentyl glycol (0.4 mole). A 40.4-g portion of triethylamine (0.4 mole) is then added dropwise at a rate such that the temperature of the stirred ingredients is maintained below 40° C. After addition is complete, stirring of the ingredients is continued for 24 hours.

The precipitated triethylammonium chloride is filtered off and the filtrate is stripped of solvent, dissolved in 200 ml $CH_2Cl_2$, washed with a saturated aqueous solution of $NaHCO_3$, then with a saturated aqueous solution of NaCl, then with $H_2O$. The organic layer is separated, dried over anhydrous $MgCl_2$, and stripped of solvent yielding a white solid.

Further purification was achieved by dissolving the solids in $CH_2Cl_2$ and cooling at ≅ −10° C. giving a very fine white precipitate. Analysis of this precipitate by nuclear magnetic resonance ($^1H$, $^{13}C$, $^{31}P$) and elemental analysis indicates that it has the following structure:

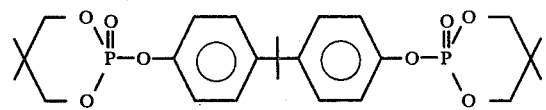

Preparation of Stabilized Polycarbonates

A 0.5-g portion of each of the aforementioned Stabilizer A, Stabilizer B and Stabilizer C is uniformly dispersed in different samples of ~5,000 g of granular homopolycarbonate of bisphenol-A having a weight average molecular weight (Mw) of about 29,000 using a conventional household mixer. The resultant blend is dried at 120° C. overnight and extruded and chopped into pellets. The extruded pellets are injection molded into test tabs and tested for melt flow characteristics, thermal resistance, hydrolytic stability and other properties indicated in Table I. The results are reported in Table I. For purposes of comparison, additional blends are similarly prepared using different amounts of Stabilizers A, B and C. The results of testing these blends are reported in Table I.

For purposes of comparison, similar polycarbonate blends are prepared using the aforementioned phosphite precursor, dimethyl pentaerythritol diphosphonate or dimethoxy pentaerythritol diphosphate as a thermal stabilizer. Test tabs are similarly prepared from the blend and tested. The results are reported in Table I.

TABLE I

| Sample No. | Thermal Stabilizer[1] | | Extrusion Stability[2] | | | Thermal Stability[3] | | Hydrolytic Stability[4] | |
|---|---|---|---|---|---|---|---|---|---|
| | Type | Amount Wt. % | ΔMFV[5] g/10 min. | ΔY[6] | ΔIzod[7] Ft. lb/in | ΔMFV[5] g/10 min. | ΔY[6] | ΔMFV[5] g/10 min. | ΔIzod[7] ft. lb/in |
| 1 | A | 0.01 | 0.4 | 2.8 | 0 | 0.9 | 5.0 | 1.9 | 0 |
| 2 | A | 0.10 | ND | 3.3 | 0.3 | 1.5 | 7.5 | 3.7 | 1.7 |
| 3 | B | 0.05 | ND | 4.9 | 0 | 1.2 | 6.7 | 1.5 | 1.2 |
| 4 | B | 0.10 | ND | 5.2 | 0.2 | 2.9 | 6.4 | 3.4 | 3.2 |
| 5 | C | 0.01 | 0.1 | 3.5 | 0 | 0.4 | 5.8 | 1.3 | 2.2 |
| 6 | C | 0.10 | 0.9 | 5.5 | 0.9 | 2.3 | 6.1 | 3.9 | 0.8 |
| $A_1$* | TEGP | 0.01 | 0.4 | 3.9 | 0.7 | 4.8 | 7.0 | 5.8 | 3.0 |
| $A_2$* | TEGP | 0.10 | 3.2 | 4.7 | 1.4 | 51.4 | 13.3 | 71.3 | 15.1 |
| $B_1$* | W-12 | 0.01 | 1.1 | 4.2 | 0.4 | 6.5 | 40.0 | 8.7 | 4.4 |
| $B_2$* | W-12 | 0.10 | 15.0 | 67.6 | 2.5 | 23.2 | 120.8 | 136.5 | 15.3 |
| $D_1$* | W-15 | 0.01 | 4.1 | 4.1 | 0.7 | 8.5 | 8.8 | 11.3 | 13.8 |
| $D_2$* | W-15 | 0.10 | 4.7 | 4.1 | 1.0 | 38.7 | 17.0 | 41.0 | 15.2 |
| $E_1$* | MI | 0.01 | 0.5 | 4.1 | 1.3 | 1.7 | 4.6 | 7.9 | 3.5 |
| $E_2$* | MI | 0.10 | ND | ND | 0.8 | 17.6 | 4.3 | 152.7 | 16.5 |

TABLE I-continued

| Sample No. | Thermal Stabilizer[1] | | Extrusion Stability[2] | | Thermal Stability[3] | | Hydrolytic Stability[4] | |
|---|---|---|---|---|---|---|---|---|
| | Type | Amount Wt. % | ΔMFV[5] g/10 min. | ΔIzod[7] ΔY[6] Ft. lb/in | ΔMFV[5] g/10 min. | ΔY[6] | ΔMFV[5] g/10 min. | ΔIzod[7] ft. lb/in |
| C* | None | — | 6.2 | 6.5   1.2 | 2.3 | 11.8 | 1.3 | 2.5 |

*Not an example of the invention.
ND—not measured
[1]A—Stabilizer A as defined hereinbefore.
B—Stabilizer B as defined hereinbefore.
C—Stabilizer C as defined hereinbefore.
TEGP—a bicyclic phosphate having the following structure:

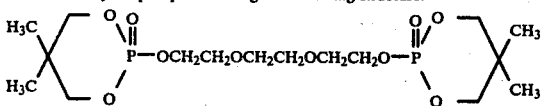

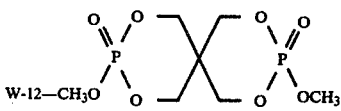

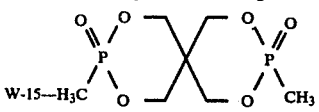

MI—see formula below:

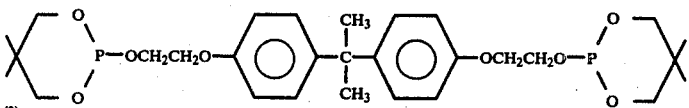

[2]Extrusion stability is the difference between measured values of sample after six extrusions from measured value of sample after one extrusion.
[3]Thermal stability is determined after heat aging at 140° C. for ~500 hours in a dry air circulating oven. The difference (Δ) is determined by subtracting the measured value of the sample after aging from the measured value of the sample before heat aging.
[4]Hydrolytic stability is determined after immersing the sample into a water bath heated to 80° C. for ~335 hours. The difference (Δ) is determined by subtracting the measured value of the sample after the immersion period from the value of the sample prior to immersion.
In general, for extrusion stability, thermal stability and hydrolytic stability, the greater numerical difference (Δ) indicates a poorer performance of the stabilizer.
[5]ASTM D-1238 (Condition O)
[6]ASTM D-1925
[7]ASTM D-256

As evidenced by the data shown in Table I, the aromatic bis(di-Y-dioxaphosphorinane) of the present invention gives substantially greater improvement of hydrolytic stability and thermal stability than do conventional stabilizers having somewhat similar structures.

What is claimed is:

1. An aromatic bis(dioxaphosphorinane) represented by the formula:

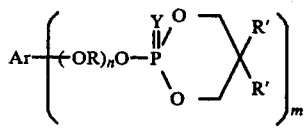

wherein Ar is a divalent aromatic radical having each of its valences on an aromatic ring; Y is oxygen or sulfur; n is 0 or a whole number up to 10; m is a whole number from 1 to 3; each R is individually a divalent aliphatic radical and each R' is individually hydrogen or a monovalent organic radical provided that the aromatic bis(-di-Y-dioxaphosphorinane) is inert to the polycarbonate.

2. The bis(dioxaphosphorinane) of claim 1 which is 2,2'-[(1-methylethylidene)bis(4,1-phenyleneoxy-2,1-ethanediyloxy)]bis(5,5-dimethyl-2,2'-dioxo-1,3,2-dioxaphosphorinane).

3. The bis(dioxaphosphorinane) of claim 1 which is 2,2'-[(1-methylethylidene)bis(4,1-phenyleneoxy-2,1-ethanediyloxy)]bis(5,5-dimethyl-2,2'-dithio-1,3,2-dioxaphosphorinane).

4. A polycarbonate composition comprising a carbonate polymer having dispersed therein the aromatic bis(dioxaphosphorinane) of claim 1 in an amount sufficient to measurably increase the thermal stability of the carbonate polymer.

5. The composition of claim 4 wherein the amount is in the range from about 0.001 to about 1 weight percent of bis(dioxaphosphorinane) based on the weight of the carbonate polymer.

6. The composition of claim 4 or 5 wherein the bis(dioxaphosphorinane) is as defined in claim 2 and the carbonate polymer is as homopolycarbonate of bisphenol-A.

7. The composition of claim 4 or 5 wherein the bis(dioxaphosphorinane) is as defined in claim 3 and the carbonate polymer is a homopolycarbonate of bisphenol-A.

8. The composition of claim 1, 4, or 5 wherein the carbonate polymer is a copolymer having ester and the carbonate linkages.

* * * * *